US00PP11692P

United States Patent [19]

van Andel

[11] Patent Number: Plant 11,692

[45] Date of Patent: Dec. 12, 2000

[54] ALSTROEMERIA PLANT NAMED 'STAPRIVINA'

[75] Inventor: Jacob van Andel, Aalsmeer, Netherlands

[73] Assignee: Van Staaveren B.V., Netherlands

[21] Appl. No.: 09/226,315

[22] Filed: Jan. 6, 1999

[51] Int. Cl.[7] ..... A01H 5/00

[52] U.S. Cl. ..... Plt./309

[58] Field of Search ..... Plt./309

[56] References Cited

PUBLICATIONS

UPOV–ROM, 1999/02, Plant Variety Database, GTI Jouve Retrieval Software, 2 citations for 'Staprivina', 1 citation for 'Staprirana'.

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 82D75-1 as seed parent and 87G1069-2 as pollen parent. The varietal denomination of the new variety is 'Staprivina'.

The first act of asexual reproduction of 'Staprivina' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Staprivina' are firmly fixed and retained through successive generations.

SUMMARY OF THE INVENTION

The new variety of Alstroemeria, 'Staprivina', produces large flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Staprivina' has not been observed under all possible environmental conditions. Phenotypic expression may vary with variations in environment such as temperature, light intensity, day length and growing and cultural conditions.

Botanical classification:

*Family.*—Amaryllidaceae.

*Genus.*—Alstroemeria sp.

Plant:

*Form.*—Bush.

*Shape.*—Upright.

*Main stem.*—About 20 to 45 cm.

*Internode length.*—About 0.5 to 2.0 cm.

*Growth.*—Vigorous.

*Strength.*—Strong.

*Blooming habit.*—Continuous.

*Rhizomes.*—Plant about 1 to 2 years old. Color: Near 155D. Size: About 10 to 30 cm.

Foliage:

*Number of leaves.*—About 10 to 20 per stem.

*Size of leaf.*—Length: About 2 to 10 cm. Width: About 1 to 3 cm.

*Shape of leaf.*—Elliptic.

*Margin.*—Straight, entire.

*Texture.*—Glossy.

*Color.*—Upper side: Near 137A. Underside: Near 137C.

Flower:

*Blooming habit.*—Continuous, blooms profusely throughout the year.

*Size (when first anthers release pollen).*—Diameter: About 6 cm. Depth: About 5 cm.

*Borne.*—About 3 to 6 flowers per umbel.

*Shape or form.*—When bloom first opens: Cup. When bloom matures: Cup.

*Fragrance.*—None.

*Lasting quality.*—On plant: About 4 weeks. As cut flower: About 18–20 days.

*Tepalage.*—Number of tepals: About 6. Arrangement: 2 concentric circles of 3 tepals. Shape: Obovate. Margin: Minutely crimped. Apex: Pointed. Texture: Soft. Appearance: Velvety.

*Color.*—Outer tepals: Body near 37A; base near 37D; underside near 37A; no spots; central distal portion darker, more intense reddish coloration, near 55A, along with a small area of green. Inner lateral tepals: Upper surface — Base near 4C, body near 4A and 37A, about 20–30 spots, spots near 185A; Undersurface — Base near 4C, body near 4C and 37A. Inner median tepal: Upper surface — Base near 4C, body near 4A and 37A, about 10–20 spots, spots near 185A; Under surface — Base near 4A, body near 4C and 37A. General: Outer tepals obovate, inner tepals long obovate, yellow lateral regions. Main stem about 20 to 45 cm.

Flower stem:

*Peduncle length.*—About 1 to 5 cm. Color: Near 137B. Strength: Strong, erect. Discoloration: No discoloration after full bloom, not hairy.

*Disease resistance.*—Unknown.

Bud:

*Size.*—Diameter: About 1 to 2 cm. Depth or length: About 2 to 4 cm.

*Form.*—Pear-shaped.
*Rate of opening.*—Fast.
*Color of tepals when tepals first divide.*—Near 37A.
*Color of tepals when tepals begin to unfurl.*—Near 37A.

Reproductive organs:
*Stamen.*—Number: About 6. Arrangement: Side by side around the style.
*Anthers.*—Size: About 8 to 10 mm. Color: Near 166D.
*Filaments.*—Length: 5 cm. Color: Near 37A.
*Pollen.*—Color: Near 177A.
*Pistils.*—1. Styles: Length about 4 to 5 cm. Color: Near 37A.
*Stigmas.*—Color: Near 37A.

Fruit: Fertile.
*Shape.*—Round.
*Color at maturity.*—Near 163A.

I claim:

1. A new and distinct Alstroemeria plant of the variety substantially as shown and described.

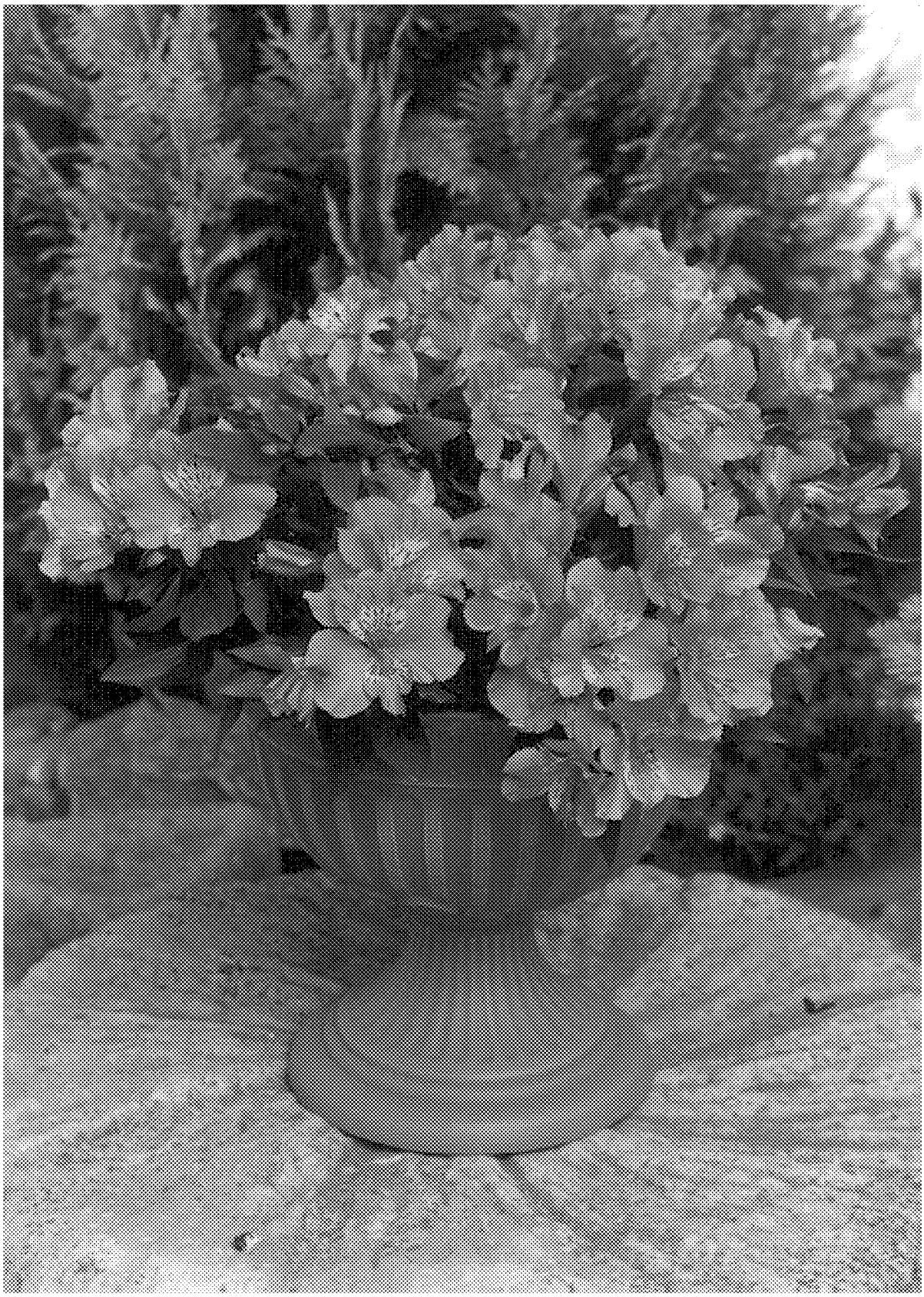

* * * * *